United States Patent [19]

Fürst et al.

[11] 4,305,881

[45] Dec. 15, 1981

[54] PROCESS FOR 1α,3β-DIHYDROXY-Δ⁵-STEROIDS

[75] Inventors: Andor Fürst, Basel; Ludwig Labler, Allschwil; Werner Meier, Bottmingen, all of Switzerland

[73] Assignee: Hoffmann-La Roche Inc., Nutley, N.J.

[21] Appl. No.: 93,209

[22] Filed: Nov. 13, 1979

[30] Foreign Application Priority Data

Nov. 17, 1978 [LU] Luxembourg .......................... 80545

[51] Int. Cl.³ ................................................. C07J 9/00
[52] U.S. Cl. ........................... 260/397.2; 260/239.55 R
[58] Field of Search ........................ 260/239.55, 397.2

[56] References Cited

U.S. PATENT DOCUMENTS 3,966,777  6/1976  Mazur et al. ............... 260/239.55 R

FOREIGN PATENT DOCUMENTS 2400931  7/1974  Fed. Rep. of Germany ........................ 260/239.55
2400189  7/1975  Fed. Rep. of Germany ........................ 260/239.55
1463985  2/1977  United Kingdom ............. 260/397.2
1491296  11/1977 United Kingdom ............. 260/397.2
1508043  4/1978  United Kingdom ............. 260/397.2

OTHER PUBLICATIONS

J. Org. Chem., 39, 2931-2933 (1974).
Tetrahedron Letters, 4 261-264 (1975).
Chemical Abstracts 80 60,077 (1974); 87 16,8276q (1977); 88 62,524 (1978); 89 24,619x (1978); 90 138,091v (1979).
Synthetic Commun. 8(2) 127-134 (1978).
J.A.C.S. (1973) vol. 95, No. 8 Article by Barton et al., pp. 2748-2749.

*Primary Examiner*—Elbert L. Roberts
*Attorney, Agent, or Firm*—Jon S. Saxe; George M. Gould; John B. Wilson

[57] ABSTRACT

A process for the synthesis of 1α,3β-dihydroxy-Δ⁵-steroids from steroids such as 1α,2α-epoxy-cholesta-4,6-dien-3-one, which is reacted with lithium in liquid ammonia in the absence of a proton donator and subsequently reduced by repeated alternative additions of a proton donator, said additions being followed in each case by an equivalent amount of lithium. The final product, a 1α,3β-dihydorxy-Δ⁵-steroid, is useful in the synthesis of derivatives of cholecalciferol.

20 Claims, No Drawings

PROCESS FOR 1α,3β-DIHYDROXY-Δ⁵-STEROIDS

BACKGROUND OF THE INVENTION

The steroid compounds to which this invention relates are intermediates useable in the synthesis of derivatives of cholecalciferol (Vitamin D₃). In particularly the invention relates to the synthesis of intermediates useable for the synthesis of 1α-hydroxy or 1α,25-dihydroxy-cholecalciferol which has been shown to possess advantageous therapeutic properties [DeLuca, et.al., Physiological Reviews 53, 327(1973)]. U.S. Pat. No. 3,901,928 relates to the preparation of 1α,3β-dihydroxy steroid-5-ene by reacting starting compounds such as 1α,2α-epoxy-steroid-4,6-dien-3-ones with an alkali metal/liquid ammonia in the presence of a proton source.

DETAILED DESCRIPTION OF THE INVENTION

The present invention relates to a novel process and compounds thereto for the manufacture of 1α,3β-dihydroxy-Δ⁵-steroids of the partial formula

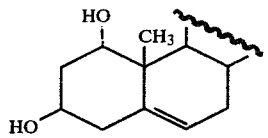

I which process comprises in a first step reducing a steroid of the partial formula

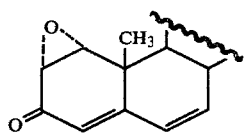

II in a solvent with at least a stoichiometric amount of lithium in liquid ammonia, in the absence of a proton donator to give a steroid of the partial formula

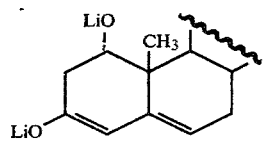

III

The unused reducing agent may be destroyed with a non-protonating agent. The steroid of partial formula III is reacted in a next step with an amount of a proton donator substantially equivalent stoichiometrically to the amount of lithium added in the first step to give a steroid of the partial formula

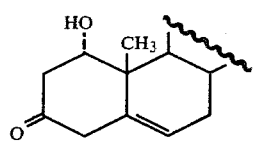

IV

In a third step the steroid of partial formula IV is reduced to give the steroid of partial formula I by repeated alternating addition of a proton donator, in each case followed by the amount of lithium substantially equivalent stoichiometrically to the amount of proton donator.

The steroids of partial formula I, especially those of the formula

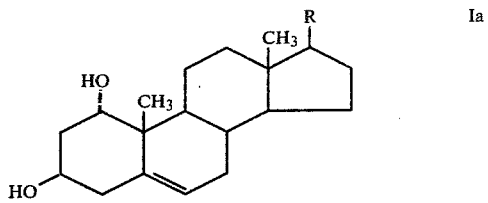

Ia wherein R represents a cholesterol side-chain optionally substituted by one or more oxygen functions, an optionally protected keto or acetyl group or a group of the formula

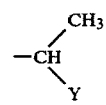

in which Y represents a hydroxy, hydroxymethyl or readily cleavable etherified hydroxy or hydroxymethyl group, are intermediates for the manufacture of derivatives of cholecalciferol (vitamin D₃), for example of 1α-hydroxy- or 1α,25-dihydroxy-cholecalciferol. The conversion of a steroid of partial formula I into these derivatives of cholecalciferol can be carried out in a manner known in the art to which this invention relates, for example, in accordance with the syntheses described in German Offenlegungsschriften Nos. 2,607,322 and 2,746,107.

The steroid starting materials of partial formula II which correspond to the steroids of formula Ia, namely those of the general formula.

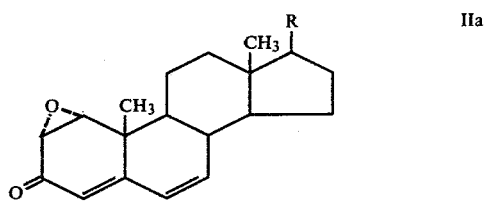

IIa wherein R has the significance given earlier, are preferred. Examples of steroids of formula IIa are those in which R represents a group of the formula

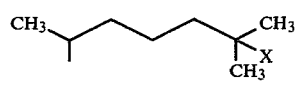

wherein X represents a hydrogen atom or a hydroxy group or, especially, a readily cleavable etherified hydroxy group, such as
1α,2α-epoxy-cholesta-4,6-dien-3-one,
1α,2α-epoxy-25-hydroxy-cholesta-4,6-dien-3-one,
1α,2α-epoxy-25-tetrahydropyranyloxy-cholesta-4,6-dien-3-one and
1α,2α-epoxy-25-(1-ethoxyethoxy)-cholesta-4,6-dien-3-one.

Examples of steroids of formula IIa in which R represents a group of the formula

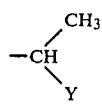

wherein Y has the significance given earlier are
(20S)-1α,2α-epoxy-20-methyl-21-tetrahydropyranyloxypregna-4,6-dien-3-one,
(20S)-1α,2α-epoxy-21-(1-ethoxyethoxy)-20-methyl-pregna-4,6-dien-3-one,
(20S)-1α,2α-epoxy-21-hydroxy-20-methyl-pregna-4,6-dien-3-one,
(20S)-1α,2α-epoxy-21-(1-methoxy-1-methylethoxy)-20-methyl-pregna-4,6-dien-3-one,
(20R)-1α,2α-epoxy-20-[(tetrahydro-2H-pyran-2-yl) oxyl]-pregna-4,6-dien-3-one and
(20R)-1α,2α-epoxy-20-hydroxy-pregna-4,6-dien-3-one.

Examples of steroids of formula IIa in which R represents an optionally protected keto or acetyl group are 17,17-ethylenedioxy-1α,2α-epoxy-androsta-4,6-dien-3-one and
20,20-ethylenedioxy-1α,2α-epoxy-pregna-4,6-dien-3-one.

The steroids of formula Ia in which R represents a cholesterol side-chain carrying a readily cleavable etherified hydroxy group in the 25-position, e.g. 1α,3β-dihydroxy-25-tetrahydropyranyloxy-cholest-5-ene, 25-(1-ethoxyethoxy)-1α,3β-dihydroxy-cholest-5-ene and the steroids of the general formula

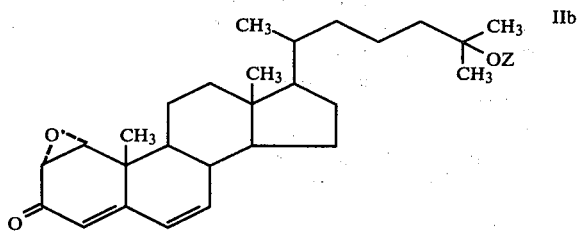

wherein OZ represents a readily cleavable etherified hydroxy group,
are novel and also form part of the present invention.

Examples of oxygen functions which can be present in the group R in the steroids of formulae Ia and IIa are hydroxy or readily cleavable etherified hydroxy groups.

Ether groups which can be cleaved readily, i.e. without other positions of the molecule being affected, are, for example, groups of the formula R$^3$O—C(R$^1$, R$^2$)-O- in which R$^1$ and R$^2$ each represents a hydrogen atom or a C$_{1-6}$-alkyl group and R$^3$ represents a C$_{1-6}$-alkylene group, such as tetrahydropyran-2-yloxy, 1-ethoxyethoxy or 1-methoxy-1-methylethoxy.

A keto or acetyl group denoted by R can be present in protected form, especially in ketalised form (e.g. in the form of the ethylene ketal).

The process for the manufacture of a steroid of partial formula I from a steroid of partial formula II is conveniently carried out in an argon atmosphere at a temperature between −30° C. and −55° C., preferably between −31° C. and −33° C. (i.e. at the boiling point of ammonia).

In the reduction of a steroid of partial formula II to a steroid of partial formula III with lithium in liquid ammonia, the steroid starting material of partial formula II is conveniently dissolved in a solvent. Any conventional art recognized inert organic solvent may be utilized in carrying out this reaction. The preferred solvent is an ether, such as diethyl ether, tetrahydrofuran or mixtures thereof; while the most preferred is absolute diethyl ether.

The reduction of a steroid of partial formula II to a steroid of partial formula III is conveniently carried out using 4 to 7 equivalents, preferably using somewhat more than the stoichiometric amount, i.e. using 4.5 to 5 equivalents, of lithium pro equivalent of steroid of partial formula II. Unused reducing agent, i.e. lithium in liquid ammonia, is destroyed, if necessary, with a non-protonating agent such as bromobenzene or, preferably, isoprene. It is essential that the reduction of a steroid of partial formula II to a steroid of partial formula III is carried out in the absence of a proton donator such as water, alcohols or ammonium salts. A steroid of partial formula III is converted into a steroid of partial formula IV by adding an amount of a proton donator equivalent to the amount of lithium used for the reduction, the preferred proton donator being an ammonium salt, especially ammonium chloride.

In the reduction of a steroid of partial formula IV to a steroid of partial formula I, care must be taken to prevent its prior conversion into salt of partial formula III which can not be reduced using lithium in ammonia. This is achieved by repeating additions of proton donator in some amount in excess of the amount of the steroid of partial formula II, with each addition followed by an amount of lithium equivalent to the amount of proton donator. Preferably the individual additions can amount to 0.3 to 6 equivalents pro equivalent of steroid of partial formula II, and the number of additions made can be 5 to 30 depending on the amount of equivalents with a total of 9 to 30 equivalents of proton donator or lithium pro equivalent of steroid of partial formula II, respectively, being conveniently and preferably used. A ten-fold to twenty-fold, especially a sixteen-fold, addition in each case of one equivalent of proton donator or lithium, respectively, is preferred.

Ether starting materials of partial formula II can be prepared in a manner known in the chemical arts, for example, by etherifying a corresponding alcohol or by etherifying a corresponding, 1,4,5-trien-3-one and subjecting the product obtained to 1,2-epoxidation. The etherification can be carried out, for example, in a solvent such as benzene with a vinyl ether (e.g. 3,4-dihydro-2H-pyran or ethyl vinyl ether) in the presence of anhydrous p-toluenesulphonic acid, conveniently at room temperature.

The following Examples illustrate the present invention and are not indended to limit the invention in scope or spirit.

EXAMPLE 1

A solution of 3.0 g (1 equivalent) of 1α,2α-epoxy-cholesta-4,6-dien-3-one in 200 ml of absolute ether is added dropwise within 45 minutes with stirring in an argon atmosphere at −31° C. to −33° C. to a solution of 210 mg (4 equivalents) of lithium in 300 ml of liquid ammonia, the liquid ammonia having been dried over sodium and distilled. As soon as the resulting mixture becomes light blue in colour the dropwise addition is quickly interrupted and 52.5 mg (1 equivalent) of lithium are added. After completion of the dropwise addition, the mixture containing cholesta-3,5-diene-1α,3β-diol dilithium salt, is stirred for 15 minutes, the blue colour is removed from the solution by the addition of 0.2 ml of isoprene and, with stirring, a total of 2.025 g 5 equivalents) of ammonium chloride are added in portions within 4 minutes. The resulting stirred yellowish mixture is treated under argon at $-31°$ C. to $-33°$ C. in the same manner with 2.312 g (5.7 equivalents) of ammonium chloride, and then with 298 mg (5.7 equivalents) of lithium; and as soon as these additions have reacted, the same procedure, i.e. the addition of 5.7 equivalents of ammonium chloride followed by 5.7 equivalents of lithium, is repeated a further four times. The mixture is thereafter treated with 10 g of ammonium chloride, and ammonia is evaporated until the temperature of the mixture has reached 0° C. The suspension is treated with 50 ml of saturated ammonium chloride solution and, after dilution with 200 ml of water, is extracted with ethyl acetate. The organic phase is dried over sodium sulphate and concentrated at 40° C./11 Torr. The crude product, 3.3 g, is chromatographed on a column of 60 g of silica gel prepared in hexane/ether (9:1). Elution with 400 ml of hexane/ether (4:1) and 1.3 liters of hexane/ether (1:1) yields 0.55 g of apolar fractions and with 2.5 liters of ether yields 2.472 g (81%) of crystalline 1α-hydroxycholesterol. After recrystallisation from acetone, this substance melts at 157°–159° C.; $[α]_D^{25} = -39.6°$ (c=0.5 in chloroform).

EXAMPLE 2

Following the procedure described in Example 1 replacing absolute ether with absolute tetrahydrofuran yields 2.242 g (73.4%) of 1α-hydroxy-cholesterol.

EXAMPLE 3

Following the procedure described in Example 1 replacing 300 ml of liquid ammonia with 150 ml of liquid ammonia yields 2.585 g (84.6%) of 1α-hydroxycholesterol.

EXAMPLE 4

8.75 g (1.26 g-atom) of lithium are added to 5 liters of dry liquid ammonia at $-31°$ C. to $-33°$ C. with stirring in an argon atmosphere resulting in a dark blue mixture. After 10 minutes, a solution of 100.0 g (0.25 mol) of 1α,2α-epoxy-cholesta-4,6-dien-3-one in 6.0 liters of absolute ether is added dropwise to the mixture during 45 minutes and subsequently the mixture is stirred for a further 15 minutes. 25.5 ml of isoprene are added dropwise to the still dark blue mixture until the colour changes to light yellow and then 67.43 g (1.26 mol) of ammonium chloride are added in portions. 13.48 g (0.25 mol) of ammonium chloride are added and then 1.75 g (0.25 g-atom) of lithium are added.

As soon as the lithium has dissolved, this procedure, i.e. the addition of 0.25 mol of ammonium chloride and 0.25 g-atom of lithium, is repeated a further fifteen times, for which a further 202.30 g (3.75 mol) of ammonium chloride and 26.25 g (3.75 g-atom) of lithium are required. As soon as the lithium of the last addition has dissolved, 100 g (1.87 mol) of ammonium chloride are added. 5 liters of ether are added dropwise to the mixture. Ammonia is evaporated by stirring overnight at room temperature. 6 liters of water and then 12 liters of ether are added to the remaining suspension. After stirring thoroughly, the organic phase is separated and the aqueous phase is extracted twice with 10 liters of ethyl acetate each time. The organic extracts are washed twice with 5 liters of saturated sodium chloride solution each time. The ether and the ethyl acetate phases are separately dried over sodium sulphate, concentrated, combined and freed from residual solvent. After drying for 18 hours at room temperature under a water-jet vacuum, 104.7 g of crude product (1α,3β-dihydroxycholest-5-ene) are obtained in the form of a yellow-brown solid.

The aforesaid 104.7 g of crude product are dissolved in 1.5 liters of pyridine and, after the addition of 1.5 liters of acetic anhydride and 1.44 g of 4-dimethylaminopyridine, the resulting mixture is stored at room temperature for 48 hours. Thereafter the mixture is poured on to 10 kg of ice and the product is extracted three times with 4 liters of ether per each extraction. The extracts are washed with 6 liters of 2 N hydrochloric acid, twice with 6 liters of water, then with 6 liters of saturated sodium bicarbonate solution, and finally twice with 6 liters of saturated sodium chloride solution. Thereafter the extracts are combined, dried over sodium sulphate, and then evaporated. The brown oily residue (134 g) is chromatographed on a column of 2.7 kg of silica gel prepared in hexane/ether (9:1). By elution with 16 liters of an hexane/ether (9:1) solvent 2.8 g of apolar fractions are obtained initially. Subsequent elution with 23 liters of the same solvent yields, after concentration and drying for 24 hours at 30° C./0.05 Torr, 101.6 g (82.7% based on 1α,2α-epoxy-cholesta-4,6-dien-3-one) of pure 1α,3β-diacetoxy-cholest-5-ene of melting point 95°–96° C.; $[α]_D^{25} = -17.1°$ (c=1.0 in chloroform).

EXAMPLE 5

A solution prepared by adding 201 mg (29 mg-atom, 4 equivalents) of lithium to 290 ml of liquid ammonia at $-33°$ C. under argon is stirred for 5 minutes and then during 45 minutes a solution of 3.0 g (7.27 mmol, 1 equivalent) of 1α,2α-epoxy-25-hydroxy-cholesta-4,6-dien-3-one in 173 ml of dry tetrahydrofuran is added dropwise with stirring in an argon atmosphere. Twice during the dropwise addition, when the resulting mixture is only just light blue in colour, 50 mg (7.2 mg/atom, 1 equivalent) of lithium are added. After completion of the dropwise addition, the mixture is stirred for 15 minutes, then the blue colour is removed from the mixture by treatment with 2 drops of isoprene and, with stirring, a total of 2.321 g (43.4 mmol, 6 equivalents) of ammonium chloride is added in portions. The resulting stirred orange-yellow mixture is treated in portions under argon at $-33°$ C. with a total of 2.222 g (41.5 mmol, 5.7 equivalents) of ammonium chloride, and then with 288 mg (41.5 mg-atom, 5.7 equivalents) of lithium, and as soon as these additions have reacted, the same procedure, i.e. the addition of 5.7 equivalents of ammonium chloride followed by 5.7 equivalents of lithium, is repeated a further four times. The mixture is then treated with 9.6 g (170 mmol, 23 equivalents) of ammonium chloride and ammonia is evaporated until the temperature of the mixture has reached 0° C. The suspension is treated with 0.5 liter of saturated sodium chloride solution, extracted once with 1 liter of ether and then twice with 2 liters of ethyl acetate. The organic extracts are washed twice with 0.5 liter of saturated sodium chloride solution, combined, dried over sodium sulphate and concentrated at 40° C./11 Torr. The concentrated residue is dissolved in 10 ml of benzene and chromatographed on a column of 30 g of silica gel prepared in hexane/ether (9:1). Elution (a) with 1.05 liters of hexane/ether (1:1) yields 1.21 g of apolar fractions, (b) with 2.4 liters of ether yields 1.94 g (63.7%) of crystalline 1α,3β,25-trihydroxy-cholest-5-ene and (c) with 1 liter of acetone yields 0.2 g of polar fractions. The product obtained from elution (b) melts, after recrystallisation from acetone, at 168°–173° C.; $[\alpha]_D^{25} = -11°$ (c=1.0 in methanol).

EXAMPLE 6

Following the procedure described in Example 5 replacing tetrahydrofuran with ether/tetrahydrofuran (10:5:1) yields 2.0 g (64.8%) of 1α,3β, 25-trihydroxy-cholest-5-ene.

EXAMPLE 7

The Preparation of The Starting Material 13 ml of benzene are distilled off from a solution of 0.7 g of 1α,2α-epoxy-25-hydroxy-cholesta-4,6-dien-3-one in 33 ml of benzene and the residue is treated with 0.4 ml of 3,4-dihydro-2H-pyran and 3.9 mg of anhydrous p-toluene-sulphonic acid. After standing at room temperature for 4 hours, the mixture is diluted with 50 ml of ether, washed with 30 ml of saturated sodium hydrogen carbonate solution and 60 ml of saturated sodium chloride solution, and then dried over sodium sulphate and concentrated. The resulting yellow, oily residue yields, after chromatography on 30 g of silica gel with hexane/ether (4:1), 0.79 g (93.7%) of 1α,2α-ethoxy-25-tetrahydropyranyloxy-cholesta-4,6-dien-3-one. After recrystallization from hexane, this product melts at 67°–69° C.; $[\alpha]_D^{25} = +154°$ (c=1.0 in chloroform).

The Process

To 2.7 liters of dry liquid ammonia are added under argon in 30 portions 1.873 g (0.27 g-atom) of lithium with stirring. After 2.5 minutes, the solution, which has become deep blue, is treated dropwise with an epoxide solution of 33.6 g (ca 67.7 mmol) of 1α,2α-epoxy-25-tetrahydropyranyloxy-cholesta-4,6-dien-3-one in 1.6 liters of ether. After the addition of three quarters of the epoxide solution, the dropwise addition is interrupted, 0.467 g (0.067 g-atom) of lithium is added in several portions and the dropwise addition is continued. 120 ml of ether is added, the solution is stirrred for a further 15 minutes, and then 2 ml of isoprene are added dropwise. 18.04 g (0.337 mol) of ammonium chloride are then added in portions of 1 g while stirring, and, in the same manner of addition, there are added a further 20.672 g (0.38 mol) of ammonium chloride. 2.681 g (0.38 g-atom) of lithium in 5–6 portions with each new portion only being added when the preceding portion has reacted completely. The addition of 20.672 g of ammonium chloride and 2.681 g of lithium is repeated a further four times in the given sequence, for which a total of 62.016 g (1.14 mol) of ammonium chloride and 8.043 g (1.14 g-atom) of lithium are required. After completion of the last lithium addition, 50.0 g of ammonium chloride are added. After cooling the solution to 0° C., 250 ml of saturated ammonium chloride solution and then 1 liter of water are added. 2.5 liters of ether is added, the solution is thoroughly shaken and the aqueous phase is separated and extracted twice with 3 liters of ethyl acetate. The organic phases are washed twice with 500 ml of saturated sodium chloride solution. This wash solution is washed with ethyl acetate and the organic phases are combined and dried. After concentration and drying, 37 g of an orange resin are obtained. For purification, a solution of the resin in benzene is chromatographed on silica gel using ether as the eluting agent. There are obtained 22.0 g (83.8%) of 1α,3β-dihydroxy-25-tetrahydropyranyloxy-cholest-5-ene in the form of a white crystalline mass. After recrystallisation from ether, this substance melts at 130°–132° C.; $[\alpha_D^{25} = -31.3°$ C. (c=1.0 in chloroform).

EXAMPLE 8

10.77 g (1.55 g-atom) of lithium are added to 6.2 liters of dry liquid ammonia at −31° C. to −33° C. with stirring in an argon atmosphere. After 10 minutes, there is added dropwise to the resulting dark blue mixture a solution of 154.6 g of 90% pure (0.31 mol) 1α,2α-epoxy-25-tetrahydropyranyloxy-cholesta-4,6-dien-3-one in 7.4 liters of absolute ether. Thereafter the mixture is rinsed with 0.5 liter of absolute ether and subsequently stirred for a further 15 minutes. 23.5 ml of isoprene are added dropwise to the still dark blue mixture until the color changes to orange. Thereafter 82.97 g (1.55 mol) of ammonium chloride are added in portions. 16.59 g (0.31 mol) of ammonium chloride are added and then 2.15 g (0.31 g-atom) of lithium are added. As soon as the lithium has dissolved, this procedure, i.e. the addition of 0.31 mol of ammonium chloride followed by 0.31 g-at of lithium, is repeated a further fifteen times, for which a further 248.85 g (4.65 mol) of ammonium chloride and 32.25 g (4.65 g-atom) of lithium are required. As soon as the lithium of the last addition has dissolved, 100 g (1.87 mol) of ammonium chloride are added. 5 liters of ether are added dropwise to the mixture. Ammonia is evaporated by stirring overnight at room temperature. 6 liters of water and then 8 liters of ether are poured into the remaining suspension. After thorough stirring, the organic phase is separated and the aqueous phase is extracted twice with 10 liters of ethyl acetate each time. The organic extracts are washed twice with 4 liters of saturated sodium chloride solution each time. The ether and the ethyl acetate extracts are dried separately over sodium sulphate, concentrated, combined and freed from residual solvent by drying for 16 hours at room temperature under a water-jet vacuum, yielding thereby 165.5 g of crude product (1α,3β-dihydroxy-25-tetrahydro-pyranyloxy-cholest-5-ene) in the form of a yellowish-brown resin.

The foregoing crude product is chromatographed on a column of 3.1 kg of silica gel prepared in hexane/ether. By elution with ether/hexane (1:1) and ether apolar fractions are first of all removed. Subsequent elution with ether and ether/ethyl acetate (9:1), concentration and drying for 16 hours at 25° C./0.01 Torr yield 105.6 g (75.3%) of 1α,3β-dihydroxy-25-tetrahydropyranyloxy-cholest-5-ene. Subsequent elution with ether/ethyl acetate (1:1) and ethyl acetate yields 9.8 g of a residue from which, after acid hydrolysis and crystallisation, there are obtained 5.6 g (4%) of 1α,3β,25-trihydroxy-cholest-5-ene of melting point 170°–172° C.; $[\alpha]_D^{25} = -11.4°$ (c=0.5 in methanol).

EXAMPLE 9

A solution of 22.4 g (52 mmol, 1 equivalent) of (20S)-1α,2α-epoxy-20-methyl-21-tetrahydropyranyloxy-pregna-4,6-dien-3-one in 1.25 liters of absolute ether is added dropwise within 45 minutes while stirring in an argon atmoshere at −33° C. to a solution of 1.453 g (0.21 g-atom), 4 equivalents) of lithium in 2.1 liters of liquid ammonia. In so doing, when the resulting mixture is only just light blue in colour, the dropwise addition is interrupted briefly and 0.363 g (52.3 mg-atom), 1 equivalent) of lithium is added. After completion of the dropwise addition, the mixture is stirred for 15 minutes and the blue colour is removed from the mixture by the addition of 2 ml of isoprene. With stirring there are added in portions 13.98 g (0.26 mol, 5 equivalents) of ammonium chloride. The mixture is treated in portions under argon at −33° C. with 16.048 g (0.30 mol, 5.7 equivalents) of ammonium chloride, and then with 2.082 g (0.3 g-atom, 5.7 equivalents) of lithium and, as soon as these additions have reacted, the same procedure, i.e. the addition of 16.048 g of ammonium chloride followed by 2.082 g of lithium is repeated a further four times. The mixture is treated with 75 g of ammonium chloride and ammonia is evaporated until the temperature of the mixture has reached 0° C. The residue is treated with 0.2 liter of saturated sodium chloride solution and 1 liter of water, extracted with 3 liters of ether and twice with 2.5 liters of ethyl acetate. The extracts are washed twice with 0.5 liter of saturated sodium chloride solution, combined, dried over sodium sulphate and concentrated at 40° C./11 Torr. The residue is dissolved in 75 ml of benzene and added to a column of 340 g of silica gel prepared in hexane/ether (9:1). Elution (a) with 3 liters of hexane/ether (4:1) and 14 liters of hexane/ether (1:1) yield 2.39 g of apolar fractions and (b) with 19 liters of ether yields 19.7 g (86.78%) of crude (20S)-1α,3β-dihydroxy-20-methyl-21-tetrahydropyranyloxy-pregn-5-ene. Recrystallisation from methanol gives white crystals of melting point 138°–141° C.; $[\alpha]_D^{25} = -48.8°$ (c=0.5 in chloroform).

EXAMPLE 10

The Preparation of the Starting Material 1.0 g (2.42 mmol) of 1α,2α-epoxy-25-hydroxy-cholesta-4,6-dien-3-one are dissolved in 60 ml of absolute toluene containing 5.0 mg of anhydrous p-toluenesulphonic acid, 10 ml of solvent are removed in vacuo and the residue is treated at room temperture with 2 ml (1.5 g, 20 mmol) of ethyl vinyl ether. The resulting mixture is left at room temperature for 1 hour, 0.3 ml of triethylamine is added and the mixture is evaporated in vacuo. The partially crystalline residue gives, after chromatography on 15 g of silica gel with hexane/ether (4:1), 1,134 g (96%) of .pure 25-(1-ethoxyethoxy)-1α,2α-epoxycholesta-4,6-dien-3-one. The analytical sample is prepared by recrytallisation from a mixture of methylene chloride and hexane containing 0.1% of triethylamine; melting point 113°–120° C.; $[\alpha]_D^{25} = +161°$ (c=0.5 in chloroform); UV (ethanol): $\lambda_{max}$ 292 nm ($\epsilon=20600$).

The Process

A solution of 0.277 g (40 mg-atom) of lithium in 150 ml of dry liquid ammonia, prepared at −31° C. to −33° C., is stirred for 10 minutes and then treated dropwise within 40 minutes in an argon atmosphere with stirring with a solution of 3.52 g (7.27 mmol) of 25-(1-ethoxyethoxy-1α,2α-epoxy-cholesta-4,6-dien-3-one in 170 ml of absolute ether. After stirring for 15 minutes, 3 drops of isoprene are added to the blue solution and the resulting pink mixture is treated, while stirring and gassing with argon, first with 2,527 g (47.2 mmol) of ammonium chloride in portions and then with 0.050 g (7.27 mg-atom) of lithium. As soon as the lithium has dissolved, 0.389 g (7.27 mmol) of ammonium chloride and then a further 0.0504 g (7.27 mg-atom) of lithium are added. This procedure, i.e. the addition of 7.27 mmol of ammonium chloride followed by 7.27 mg-atom of lithium, is repeated a further fourteen times, for which a total of 5.446 g (101.8 mmol) of ammonium chloride and 0.706 g (101.8 mg-atom) of lithium are required. As soon as the lithium of the last addition has dissolved, 5.8 g (93 mmol) of ammonium chloride are added, then 70 ml of ether are added and ammonia is evaporated while stirring. The residual suspension is treated with water and extracted with ether. The organic phases are washed with saturated sodium chloride solution, dried over sodium sulphate and evaporated in vacuo. The residue is chromatographed on a column of 60 g of silica gel prepared with hexane/ether (9:1) containing 0.4% pyridine. Elution with hexane/ether (1:1) and ether yields 2.621 g (73.4%) of pure 25-(1-ethoxyethoxy)-1α,3β-dihydroxy-cholest-5-ene in the form of a colourless powder of melting point 128°–130° C.; $[\alpha]_D^{25} = -30.5°$ (c=1.0 in chloroform containing 0.1% triethylamine).

EXAMPLE 11

The Preparation of the Starting Material

In a manner analogous to that described in Example 10, from 0.215 g (0.62 mmol) of (20S)-1α,2α-epoxy-21-hydroxy-20-methylpregna-4,6-dien-3-one there is obtained 0.234 g (90% of theory) of (20S)-21-(1-ethoxyethoxy)-1α,2α-epoxy-20-methylpregna-4,6-dien-3-one; melting point 91°–93° C.; $[\alpha]_D^{25} = +177°$ (c=0.5 in chloroform containing 0.5% triethylamine); UV (ethanol): $\lambda_{max}$ 292 nm ($\epsilon=21080$).

The Process

A solution of 0.308 g (44 mg-atom) of lithium in 170 ml of dry liquid ammonia, prepared at −31° C. to −33° C., is stirred for 10 minutes and then with stirring is treated dropwise within 40 minutes in an argon atmosphere with a solution of 3.67 g (8.87 mmol) of (20S)-21-(1-ethoxyethoxy)-1α,2α,epoxy-20-methyl-pregna-4,6-dien-3-one in 210 ml of absolute ether. After stirring for 15 minutes, 0.2 ml of isoprene are added to the blue solution, resulting in an almost colourless mixture. With stirring and gassing with argon, to the mixture is added first 2.849 g (52.9 mmol) of ammonium chloride in portions and then 0.061 g (8.8 mg-atom) of lithium. As soon as the lithium has dissolved, 0.475 g (8.8 mmol) of ammonium chloride and then a further 0.061 g (8.8 mg-atom) of lithium are added. This procedure, i.e. the addition of 8.8 mmol of ammonium chloride followed by 8.8 mg-at of lithium, is repeated a further fourteen times, for which a total of 6.65 g (124.3 mmol) of ammonium chloride and 0.854 g (124 mg-atom) of lithium are required. As soon as the lithium of the last addition had dissolved, a further 5.0 g (93 mmol) of ammonium chloride are added, and then 80 ml of ether are added and ammonia is evaporated with stirring. The residual suspension is diluted with water and extracted with ether. The extract is washed with saturated sodium chloride solution, dried over sodium sulphate and evaporated in vacuo. The residue is chromatographed on 60 g of silica gel [prepared with hexane/ether (9:1) containing 0.4% pyridine]. Elution with ether gives 2.877 g (76.8%) of (20S)-21-(1-ethoxyethoxy)-1α,3β-dihydroxy-20-methyl-pregn-5-ene in the form of a colourless amorphous powder of melting point 124°–126° C.; $[\alpha]_D^{25} = -43.3°$ C. (c=1.0 in chloroform containing 0.1% triethylamine).

EXAMPLE 12

0.334 g (48 mg-atom) of lithium are added while stirring and gassing with argon to 170 ml of dry liquid ammonia at −31° C. to −33° C. The resulting dark blue mixture is stirred for 15 minutes and then treated dropwise within 40 minutes with a solution of 3.0 g (8.76 mmol) of (20S)-1α,2α-epoxy-21-hydroxy-20-methyl-pregna-4,6-dien-3-one in 208 ml of ether/tetrahydrofuran (4.2:1). After stirring for an additional 15 minutes, 0.2 ml of isoprene are added to the blue mixture and the resulting pink mixture is subsequently treated, while stirring and gassing with argon, first with 3.045 g (57 mmol) of ammonium chloride in portions and then with 0.0608 g (8.7 mg-atom) of lithium. As soon as the lithium has dissolved, 0.468 g (8.7 mmol) of ammonium chloride and then a further 0.0608 g (8.7 mg-atom) of lithium are added. This procedure, i.e. the addition of 8.7 mmol of ammonium chloride followed by 8.7 mg-atom of lithium, is repeated a further fourteen times, for which a total of 6.552 g (122 mmol) of ammonium chloride and 0.851 g (122 mg-atom) of lithium are required. As soon as the lithium of the last addition has dissolved, 10.8 g (180 mmol) of ammonium chloride and then 150 ml of ether are added, and the ammonia is evaporated with stirring. The resulting suspension is diluted at 0° C. with 200 ml of water and extracted with ethyl acetate. The extract is washed with saturated sodium chloride solution, dried over sodium sulphate and evaporated at 40° C./11 Torr. Chromatography of the residue on 90 g of silica gel with benzene/ethyl acetate (1:1) and ethyl acetate yields 1.93 g (63%) of uniform, crystalline (20S)-1α,3β,21-trihydroxy-20-methyl-pregn-5-ene of melting point 205°–207° C.; $[\alpha]_D^{25} = -25.8°$ (c=0.5 in methanol). The analytical sample is prepared by recrystallisation from acetone; melting point 206°–208° C., $[\alpha]_D^{25} = -27°$ (c=0.5 in methanol).

EXAMPLE 13

The Preparation of the Starting Material

A solution of 3.42 g (10 mmol) of (20S)-1α,2α-epoxy-21-hydroxy-20-methyl-pregna-4,6-dien-3-one in 100 ml of toluene is concentrated to 50 ml in a water-jet vacuum. The resulting suspension is treated at 0° C. with 2 ml of a suspension prepared from 50 ml of toluene, 0.172 g of p-toluenesulphonic acid and 0.2 ml of pyridine. Thereafter 3 ml of isopropenyl methyl ether are added and the resulting mixture is stirred at 0° C. for 3 hours. After the addition of 1 ml of triethylamine, the mixture is concentrated at 30° C./11 Torr. The crystalline residue is dissolved in a small amount of methylene chloride containing 0.1% triethylamine and treated with ether to give 2.91 g (70%) of (20S)-1α,2α-epoxy-21-(1-methoxy-1-methylethoxy)-20 -methyl-pregna-4,6-dien-3-one of melting point 150°–151° C.; $[\alpha]_D^{25} = +185.8°$ C. (c=1.0 in chloroform containing 0.1% triethylamine).

The Process

A solution of 0.416 g (60 mg-atom) of lithium in 200 ml of dry liquid ammonia, prepared at −31° to −33° C., is stirred for 10 minutes and then treated dropwise within 40 minutes in an argon atmosphere with stirring with a solution of 4.14 g (10 mmol) of (20S)-1α,2α-epoxy-21-(1-methoxy-1-methylethoxy)-20-methyl-pregna-4,6-dien-3-one in 240 ml of ether/tetrahydrofuran (1.6:1). After stirring for 15 minutes, 0.5 ml of isoprene are added to the blue solution and the resulting pink mixture is, with stirring and gassing with argon, first treated with 3.744 g (70 mmol) of ammonia chloride in portions and then with 0.069 g (10 mg-atom) of lithium. As soon as the lithium has dissolved, 0.535 g (10 mmol) of ammonium chloride is added and then a further 0.069 g (10 mg-atom) of lithium is added. This procedure, i.e. the addition of 10 mmol of ammonium chloride followed by 10 mg-at of lithium, is repeated a further fourteen times, for which a total of 7.49 g (140 mmol) of ammonium chloride and 0.966 g (140 mg-atom) of lithium are required. As soon as the lithium of the last addition has dissolved, 10 g (180 mmol) of ammonium chloride and then 100 ml of ether are added, and ammonia is evaporated with stirring. The remaining suspension is treated at 0° C. with water and extracted with ethyl acetate. The extract is washed with saturated sodium chloride solution, dried over sodium sulphate and, after treatment with 1 ml of triethylamine, evaporated at 30° C./11 Torr. Chromatography of the residue on 140 g of neutral aluminum oxide with benzene/ethyl acetate (1:1) and ethyl acetate yields 3.01 g (71.6%) of uniform, crystalline (20S)-1α,3β-dihydroxy-21-(1-methoxy-1-methylethoxy)-20-methyl-pregn-5-ene. The analytical sample is prepared by recrystallisation from methanol containing 0.1% triethylamine; melting point 156°–157° C., $[\alpha]_D^{25} = -46°$ (c=1.0 in chloroform containing 0.1% triethylamine.

EXAMPLE 14

The Preparation of the Starting Material

A solution of 34.8 g (0.11 mol) of (20R)-20-hydroxy-pregn-4-en-3-one in 300 ml of dimethyl sulphoxide is treated with 18.7 g (0.16 mol) of potassium tert. butoxide and stirred for 4 hours at room temperature under argon. The red-brown mixture is poured on to 1 kg of ice and the product is extracted with methylene chloride. The extract is washed with water, dried over sodium sulphate and evaporated in a water-jet vacuum. The residue is chromatographed on 1 kg of silica gel with hexane/ether/methylene chloride (7:2:1) and gives 7.3 g (21%) of uniform, crystalline (20R)-20-hydroxy-pregn-5-en-3-one. The analytical sample is obtained by recrystallisation from ethanol/methylene chloride; melting point 171°–175° C.; $[\alpha]_D^{25} = -33.2°$ (c=0.5 in chloroform).

A mixture prepared from 6.7 g (21.1 mmol) of (20R)-hydroxy-pregn-5-en-3-one, 11.9 g (52.4 mmol) of 2,3-dichloro-5,6-dicyano-benzoquinone and 200 ml of dioxan is boiled at reflux for 6 hours. After cooling to room temperature, the mixture is suction-filtered, the residue is washed with dioxan and the combined filrates are filtered over 100 g of neutral aluminium oxide. The eluate is evaporated and the residue is chromatographed on 200 g of silica gel with ether. There are thus obtained 2.94 g (44.5%) of (20R)-20-hydroxy-pregna-1,4,6-trien-3-one in the form of yellowish crystals of melting point 162°–164° C.

A solution of 2.79 g (8.92 mmol) of (20R)-20-hydroxy-pregna-1,4,6-trien-3-one in 27 ml of methanol is treated with 0.83 ml of 10% methanolic sodium hydroxide, cooled to 0° C., and 5.4 ml of 30% hydrogen peroxide solution are added dropwise during 10 minutes with stirring. The solution is stirred at 0° C. for 45 minutes and then at room temperature for 3 hours. The suspension formed is treated with a total of 60 ml of water in portions, cooled to 0° C. and excess peroxide is destroyed by the addition of sodium hydrogen sulphite solution. The mixture is freed from methanol in a water-jet vacuum and the residue is extracted with ethyl acetate. The extract is washed with saturated sodium chloride solution, dried over sodium sulphate and evaporated. Chromatography of the residue on 80 g of silica gel with hexane/ether (1:1) gives 1.77 g (60.4%) of uniform (20R)-1α,2α-epoxy-20-hydroxy-pregna-4,6-dien-3-one in the form of colourless crystals. The analytical sample is obtained by recrystallisation from methylene chloride/ether; melting point 206°–207° C., $[\alpha]_D^{25}=+231.6°$ (c=0.5 in chloroform); UV (ethanol): $\lambda_{max}$ 292 nm (ε=21050).

A solution of 2.67 g (8.1 mmol) of (20R)-1α,2α-epoxy-20-hydroxy-pregna-4,6-dien-3-one in 120 ml of benzene is concentrated to 60 ml in a water-jet vacuum at 40° C., cooled to room temperature and to the suspension are added 1.6 ml of 3,4-dihydro-2H-pyran as well as 16 mg of anhydrous p-toluenesulphonic acid. The mixture is stirred at room temperature for 2.5 hours. The resulting solution is diluted with ether, washed with saturated sodium hydrogen carbonate solution and then with saturated sodium chloride solution, dried over sodium sulphate and evaporated. There are obtained 3.3 g of crystalline (20R)-1α,2α-epoxy-20-[(tetrahydro-2H-pyran-2-yl)oxy]-pregna-4,6-dien-3-one. Recrystallisation from ether containing 0.1% triethylamine yields colourless prisms of melting point 139°–140° C.; $[\alpha]_D^{25}=+233.6°$ (c=0.5 in chloroform), UV (ethanol): $\lambda_{max}$ 291 nm (ε=20940).

The Process 0.316 g (45 mg-atom) of lithium are added to 150 ml of dry liquid ammonia at −31° C. to −33° C. After stirring for 15 minutes in an argon atmosphere, the resulting dark blue mixture is treated dropwise within 45 minutes with a solution of 3.23 g (7.8 mmol) of (20R)-1α,2α-epoxy-20-[(tetrahydro-2H-pyran-2-yl)oxy]-pregna-4,6-dien-3-one in 180 ml of ether. The blue mixture is stirred at the aforementioned temperature for 15 minutes in an argon atmosphere and 0.15 ml of isoprene is added. The resulting pink mixture is treated with 2.845 g (53 mmol) of ammonium chloride in portions and then with 0.0527 g (7.6 mg-atom) of lithium. As soon as the lithium has dissolved, 0.4065 g (7.6 mmol) of ammonium chloride and subsequently a further 0.0527 g (7.6 mg-atom) of lithium are added. This procedure, i.e. the addition of 7.6 mmol of ammonium chloride followed by 7.6 mg-atom of lithium, is repeated a further fourteen times, for which a total of 5.691 g (106 mmol) of ammonium chloride and 0.7378 g (106 mg-atom) of lithium are required. After the lithium of the last addition has dissolved, 10.0 g (180 mmol) of ammonium chloride and 200 ml of ether are added, and ammonia is evaporated with stirring. The resulting suspension is diluted at 0° C. with 200 ml of water and extracted with ethyl acetate. The extract is washed with saturated sodium chloride solution, dried over sodium sulphate and evaporated at 40° C./11 Torr. Chromatography of the residue on 65 g of silica gel with hexane/ether (1:1) gives 2.52 g (78%) of uniform (20R)-1α,3β-dihydroxy-20-[(tetrahydro-2H-pyran-2-yl)oxy]-pregn-5-ene of melting point 122°–124° C.; $[\alpha]_D^{25}=-42°$ (c=1.0 in chloroform). By acidic hydrolysis there is obtained (20R)-1α,3β,20-trihydroxy-pregn-5-ene of melting point 235°–237° C.; $[\alpha]_D^{25}=43°$ (c=0.5 in methanol).

EXAMPLE 15

The Preparation of the Starting Material

A solution of 1.0 g of 17, 17-ethylenedioxy-androsta-1,4,6-trien-3-one in 40 ml of methanol is treated at room temperature with 0.28 ml of 10% methanolic sodium hydroxide and 1.8 ml of 30% hydrogen peroxide and stirred at room temperature for 4.5 hours. 50 ml of water are added dropwise to the solution, the separated product is collected by suction and chromatographed on 30 g of silica gel. Elution with hexane/ether (3:2) yields 0.793 g (75%) of crystalline 17,17-ethylenedioxy-1α,2α-epoxy-androsta-4,6-dien-3-one. The analytical sample is prepared by recrystallisation from ether; melting point 181°–186° C.; $[\alpha]_D^{25}=+167°$ (c=0.5 in dioxan); UV (ethanol): $\lambda_{max}$ 291 nm (ε=19270).

The Process 1.543 g (0.22 g-atom) of lithium are added to 1.3 liters of dry liquid ammonia at −31° C. to −33° C. with stirring in an argon atmosphere. After 5 minutes, there is added dropwise during 40 minutes to the resulting dark blue mixture a solution of 10.83 g (0.0316 mol) of 17,17-ethylenedioxy-1α,2α-epoxyandrosta-4,6-dien-3-one in 765 ml of ether/tetrahydrofuran (2:1). After stirring for 15 minutes, 5.3 ml of isoprene are added dropwise to the mixture. The resulting yellow mixture is treated with stirring with 13.49 g (0.252 mol) of ammonium chloride in portions and then 0.22 g (0.0316 g-atom) of lithium is added. As soon as the lithium has dissolved, 1.69 g (0.0316 mol) of ammonium chloride and subsequently a further 0.22 g (0.0316 g-atom) of lithium are added. This procedure, i.e. the addition of 0.0316 mol of ammonium chloride and 0.0316 g-at of lithium, is repeated a further fourteen times, for which a total of 23.66 g (0.442 mol) of ammonium chloride and 3.08 g (0.442 g-atom) of lithium are required. As soon as the lithium of the last addition has dissolved, 24 g (0.44 mol) of ammonium chloride are added and the mixture is cautiously diluted with 1 liter of ether. Ammonia is evaporated while stirring until an internal temperature of 0° C. has been reached and the remaining suspension is treated with 1 liter of water. The organic phase is separated, the aqueous phase is back-extracted with ethyl acetate, the organic phases are combined, washed with saturated sodium chloride solution, dried over sodium sulphate and evaporated at 40° C./11 Torr. Chromatography of the residue on 300 g of silica gel with benzene/ethyl acetate (3:2) and benzene/ethyl acetate (2:3) gives 8.8 g (80%) of uniform, crystalline 17,17-ethylenedioxy-1α,3β-dihydroxy-androst-5-ene. The analytical sample is obtained by recrystallisation from methanol; white needles of melting point 205°–206° C.; $[\alpha]_D^{25}=-89.8°$ (c=0.5 in chloroform).

EXAMPLE 16

The Preparation of the Starting Material

A solution of 50.0 g of 20,20-ethylenedioxy-3β-hydroxy-pregn-5-ene in 900 ml of dioxan is treated with 95 g of 2,3-dichloro-5,6-dicyano-1,4-benzoquinone and boiled under reflux for 20 hours. The resulting suspension is suction filtered, the residue is washed with dioxan and the combined filtrates are concentrated in vacuo to a volume of 200 ml. The concentrate is filtered over 900 g of neutral aluminium oxide, back-washed with dioxan and the combined filtrates are evaporated at 40° C. in a water-jet vacuum. The residue yields, by chromatography on 900 g of neutral aluminium oxide with hexane/ether (1:1), 9.2 g (18.7%) of 20,20-ethylenedioxy-pregna-1,4,6-trien-3-one. Recrystallisation from methanol containing 0.5% pyridine yields 6.2 g of light yellow substance, shaped like needles and with a melting point of 162°–163° C.; $[\alpha]_D^{25}=+13.6°$ (c=0.5 in chloroform), UV (ethanol): $\lambda_{max}$ 222 (ε=11750), 258 (ε=9600) and 300 nm (ε=13200).

In a manner analogous to that described in Example 15, from 8.2 g of 20,20-ethylenedioxy-pregna-1,4,6-trien-3-one there are obtained 5.28 g (60%) of 20,20-ethylenedioxy-1α,2α-epoxy-pregna-4,6-dien-3-one; melting point 137°–138° C.; $[\alpha]_D^{25} = +235°$ (c=0.5 in chloroform), UV (ethanol): $\lambda_{max}$ 292 nm ($\epsilon$=20900).

The Process

A mixture of 0.594 g (0.0856 g-atom) of lithium in 500 ml of dry liquid ammonia of −31° C. to −33° C. is prepared and stirred for 5 minutes. Then, a solution of 4.535 g (0.0122 mol) of 20,20-ethylenedioxy-1α,2α-epoxy-pregna-4,6-dien-3-one in 300 ml of ether/tetrahydrofuran (2:1) is added to the mixture dropwise under argon during 40 minutes. The resulting deep blue mixture (at −33° C.) is stirred for a further 15 minutes and treated with 2 ml of isoprene until the colour changes to yellow. A total of 4.579 g (0.0856 mol) of ammonium chloride are added in portions with stirring. To the mixture is then added 0.654 g (0.0122 mol) of ammonium chloride and subsequently 0.0849 g (0.0122 g-atom) of lithium. As soon as the lithium has dissolved, this procedure, i.e. the addition of 0.0122 mol of ammonium chloride followed by the amount of lithium equivalent thereto is repeated a further fifteen times, for which a total of 9.81 g (0.183 mol) of ammonium chloride and 1.273 g (0.183 g-atom) of lithium are required. As soon as the lithium of the last addition has dissolved, 9.5 g (0.17 mol) of ammonium chloride and then 500 ml of ether are added. Ammonia is evaporated with stirring until an internal temperature of 0° C. has been reached and the remaining suspension is treated with 500 ml of water and 500 ml of ether. The organic phase is separated and the aqueous phase is back-extracted with ethyl acetate. The organic phases are combined, washed with saturated sodium chloride solution, dried over sodium sulphate and evaporated at 40° C. in a water-jet vacuum. The residue yields, by chromatography on 150 g of silica gel with ether/tetrahydrofuran (19.1) and (4:1), 3.9 g (85%) of uniform 20,20-ethylenedioxy-1α,3β-dihydroxy-pregn-5-ene. The analytical sample is obtained by recrystallisation from methanol; melting point 203°–207° C.; $[\alpha]_D^{25} = -47°$ (c=0.5 in chloroform).

We claim:

1. A process for the preparation of 1α,3β-dihydroxy-Δ⁵-steriods of the partial formula (I):

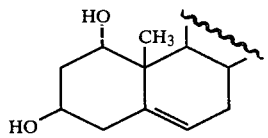

which process comprises the steps of: (A) reducing a steriod of the partial formula (II):

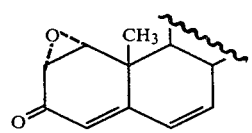

in a solvent with at least a stoichiometric amount of lithium in liquid ammonia in the absence of a portion donator, producing thereby a steroid of the partial formula (III):

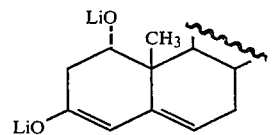

(B) reacting the steroid of partial formula III with an amount of a proton donator, which amount is substantially equivalent stoichiometrically to the amount of lithium utilized in step A, producing thereby a steroid of the partial formula (IV):

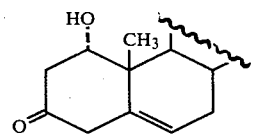

and (C) reducing the steroid of partial formula IV by repeated alternating addition of a proton donator with the addition of lithium, each addition of the proton donator being followed by the addition of lithium in an amount substantially equivalent stoichiometrically to the amount of added proton donator, producing thereby the steriod of partial formula (I).

2. A process according to claim 1, wherein a solution of the steriod of partial formula II in absolute diethyl ether is reduced with lithium in liquid ammonia.

3. A process according to claim 1, which is carried out in an argon atmosphere at a temperature between −30° C. and −55° C.

4. A process according to claim 3, which is carried out at a temperature between −31° C. and −33° C.

5. A process according to claim 1 wherein 4 to 7 equivalents of lithium in step A or of proton donator in step B, and 0.3 to 6 equivalents, a total of 9 to 30 equivalents, of proton donator is added five-times to thirty-times in step C, each addition of proton donator in step C being followed by the addition of lithium in said amount of step C.

6. A process according to claim 5, wherein 4.5 to 5 equivalents of lithium in step A or proton donator in step B are used and one equivalent of proton donator is added ten-times to twenty-times in step C, each addition of proton donator in step C being followed by the addition of lithium in said amount of step C.

7. A process according to claim 6, wherein in step C one equivalent of proton donator is added sixteen times, in each case followed by the equivalent amount of lithium.

8. A process according to claim 1 wherein an ammonium salt is used as the proton donator.

9. A process according to claim 8, wherein the ammonium salt is ammonium chloride.

10. A process according to claim 1 wherein all of the steps are carried out in the same organic solvent system.

11. A process according to claim 1 wherein, between step A and step B, unused lithium is destroyed by the addition of a non-protonating agent.

12. A process according to claim 1 wherein the reduction in step C is carried out with the proton donator being added in at least 5 additions, each addition being in increments of at least 0.3 equivalents per equivalent of the steriod of partial formula IV and each addition being followed by the addition of lithium.

13. A process according to claim 1 wherein the reduction in step C is carried out with the porton donator being added in 5 to 30 additions, each addition being in increments of 0.3 to 6 equivalents per equivalent of the steroid of partial formula IV and each addition being followed by the addition of lithium.

14. A process according to claim 1 wherein the steroid of partial formula II is a steroid of the formula (IIa):

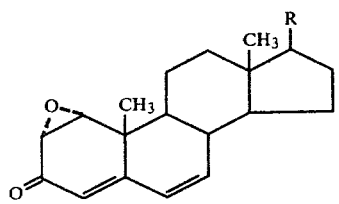

wherein R represents a cholesterol side-chain optionally substituted by one or more oxygen functions, an optionally protected keto or acetyl group or a group of the formula

in which Y represents a hydroxy, hydroxy-methyl or readily cleavable etherified hydroxy or hydroxymethyl group; or said R represents a group of the formula

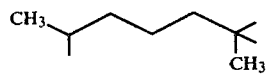

in which X represents a hydrogen atom or a hydroxy or readily cleavable etherified hydroxy group.

15. A process according to claim 14, wherein 1α,2α-epoxy cholesta-4,6-dien-3-one is used as the steriod of partial formula II.

16. A process according to claim 14, wherein 1α,2α-epoxy 25-hydroxy-cholesta-4,6-dien-3-one is used as the steroid of partial formula II.

17. A process according to claim 14, wherein 1α,2α-epoxy 25-tetrahydropyranyloxy-cholesta-4,6-dien-3-one or 25-(1-ethoxy-ethoxy)-1α,2α-epoxy-cholesta-4,6-dien-3-one is used as the steriod of partial formula II.

18. A process according to claim 14, wherein (20S)-1α,2α-epoxy-20-methyl-21-tetrahydropyranyloxy-pregna-4,6-dien-3-one; (20S)-21-(1-ethoxyethoxy)-1α,2α-epoxy-20-methyl-pregna-4,6-dien-3-one; or (20S)-1α,-2α-epoxy-21-(1-methoxy-1-methylethoxy)-20-methyl-pregna-4,6-dien-3-one is used as the steriod of partial formula II.

19. A process for the preparation of steriods of the partial formula (III):

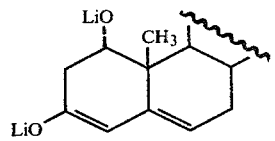

which process comprises reducing a steriod of the partial formula (II):

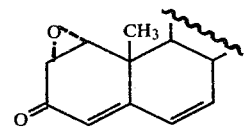

in a solvent with at least a stoichiometric amount of lithium in liquid ammonia in the absence of a proton donator, producing thereby a steriod of the partial formula (III).

20. A process for the preparation of 1α,3β-dihydroxy-Δ5-steroids of the partial formula (I):

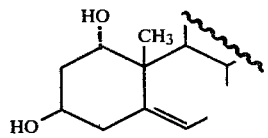

which process comprises reacting a steroid of the partial formula (III):

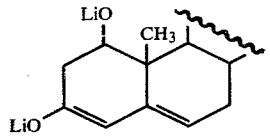

with an amount of a proton donator, which amount is substantially equivalent, stoichiometrically to the amount of lithium present in said steroid of the partial formula III, producing thereby a steroid of the partial formula (IV):

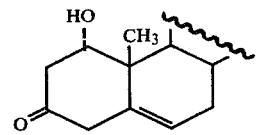

and then reducing the steroid of partial formula IV by repeated alternating addition of a proton donator with the addition of lithium, each addition of the proton donator being followed by the addition of lithium in an amount substantially equivalent stoichiometrically to the amount of added proton donator, producing thereby the steroid of partial formula (I).

* * * * *